United States Patent [19]

Borel et al.

[11] Patent Number: 4,650,675

[45] Date of Patent: Mar. 17, 1987

[54] OLIGONUCLEOTIDE CONJUGATES

[75] Inventors: Yves Borel, Brookline; B. David Stollar, Newton; Helina Borel, Brookline; Paul M. Gallop, Chestnut Hill, all of Mass.

[73] Assignee: The Children's Medical Center Corporation, Boston, Mass.

[21] Appl. No.: 524,298

[22] Filed: Aug. 18, 1983

[51] Int. Cl.[4] .......................................... A61K 39/395
[52] U.S. Cl. ..................... 424/85; 530/389; 530/391
[58] Field of Search ............... 260/112 R; 424/85, 88; 536/27-29; 435/91; 530/387

[56] References Cited

U.S. PATENT DOCUMENTS

| | | | |
|---|---|---|---|
| 3,725,545 | 4/1973 | Maes | 424/180 |
| 3,821,193 | 6/1974 | Fare et al. | 536/27 |
| 4,372,883 | 2/1983 | Matuhashi et al. | 424/88 |
| 4,388,306 | 6/1983 | Field et al. | 424/85 |
| 4,400,375 | 8/1983 | Douthort et al. | 424/85 |
| 4,460,575 | 7/1984 | d'Hinterlord et al. | 536/27 |
| 4,472,301 | 9/1984 | Buckler et al. | 424/85 |

OTHER PUBLICATIONS

Yves Borel et al. (1973), American Association for the Advancement of Science, 182 76–78.
Papalian et al. (1980) J. Clin Invest., 65 469–477.
Borel et al. (1980) Proc. Natl. Acad. Sci. 77 1593–6.
Golan et al. (1971) The Journal of Experimental Medicine, 134 1046–1061.
Molin et al. (1978) The Journal of Histochemistry and Cytochemistry 26 1053–6.
Ellis et al. (1976) Progress in Medicinal Chemistry, 13 272–301.
Hopwood, David, Histochemical Journal, 7 (1975) 267–276.

*Primary Examiner*—Blondel Hazel

[57] ABSTRACT

Conjugate composed of an oligonucleotide covalently bonded to a carrier.

4 Claims, 2 Drawing Figures

——— ABSORBANCE AT 280 nm
------ ABSORBANCE AT 260 nm

OLIGONUCLEOTIDE CONJUGATES

This invention was made in the course of work under grants or awards from the National Institutes of Health and the Kroc Foundation. The U.S. government has rights in the invention.

BACKGROUND OF THE INVENTION

This invention relates to the treatment of Systemic Lupus Erythromatosus (SLE).

SLE is a disease in which the patient produces autoantibody to a wide variety of antigens, but antibody to the patient's own DNA appears to play the dominant role in the pathogenicity of the disease.

Nucleosides have been linked to mouse IgG immunoglobulin in an attempt to make a tolerogenic conjugate, i.e., a conjugate which, when administered to an SLE patient, would inhibit the production of anti-DNA antibodies. Borel et al. (1973) Science 182, 76 reports that nucleosides were used in the attempt to make tolerogens "because it is more feasible to bind free nucleosides to a protein carrier than either double or single stranded DNA."

Papalian et al. (1980) J. Clin Inv. 65, 469 discusses the size, 20–400 base pairs, of DNA recognized by anti-DNA antibodies of SLE patients and says that "[i]nformation from these studies will ... help to define minimal requirements for the preparation of hapten-specific tolerance to nucleic acid antigens in SLE."

The linking of nucleosides to cells has also been mentioned in the literature. Borel et al. (1980) P.N.A.S. U.S.A. 77(3), 1593 says: "conceivably, oligonucleotides linked to cell surfaces might suppress antibodies to either single or double stranded DNA."

Golan et al. (1971) J. Exptl. Med. 137, 1046 says that "the induction of tolerance . . . may be strongly influenced by [the] carrier moiety", and that "among the various carriers tested, IgG was the most tolerogenic."

SUMMARY OF THE INVENTION

In general, the invention features, in a first aspect, a conjugate composed of an oligonucleotide covalently bonded to a carrier. (As used herein, "carrier" means any particle, protein, cell, or antigen to which an oligonucleotide can be covalently bonded; an oligonucleotide is a string of two or more mononucleotide units joined by a phosphoric acid bridge).

In preferred embodiments of the above first aspect of the invention, the conjugate is a tolerogenic conjugate capable of inducing tolerance in a human patient suffering from SLE composed of a heterogeneous oligonucleotide at least 8 and not more than 500 base pairs in length covalently bonded to a non-antigenic, soluble isologous protein molecule, the covalent bonding being such that the conformation of the protein is similar enough to its natural conformation to render the conjugate tolerogenic rather than antigenic; preferably the covalent bonding is via an aldehydic linkage; the isologous protein is immunoglobulin, preferably of the IgG isotype, most preferably IgG$_1$; and each protein molecule has bonded to it between 0.7 and 1.2 oligonucleotides.

In other preferred embodiments of the above first aspect of the invention, the conjugate is an immunosuppressive, non-immunogenic conjugate capable of decreasing the amount of anti-DNA antibody in a human patient suffering from SLE composed of a heterogeneous oligonucleotide at least 8 and not more than 500 base pairs in length covalently bonded to an autologous lymphocyte of the human patient; preferably the covalent bonding is via an aldehydic linkage; and the lymphocyte is a peripheral blood lymphocyte.

In other preferred embodiments of the above first aspect of the invention, the conjugate is an immunogenic, immunosuppressive conjugate capable of promoting the proliferation in vitro of suppressor T cells in cultured lymphocytes of a human patient suffering from SLE, the conjugate being composed of a heterogeneous oligonucleotide at least 8 and not more than 500 base pairs in length covalently bonded to an antigen; preferably the antigen is an antigenic protein molecule, most preferably Keyhole Limpet Haemocyanin (KLH), or a heterologous antigenic mammalian cell, most preferably a sheep red blood cell (SRBC); and where KLH is the antigen, each KLH molecule has bonded to it between 5 and 20 oligonucleotides.

In a second aspect, the invention features, in general, a method of producing a nucleic acid specific suppressor T cell capable of producing a soluble immunosuppressive factor capable of improving the medical condition of a human patient suffering from SLE, the method including obtaining a sample of lymphocytes from the patient, culturing the sample of lymphocytes in the presence of an immunosuppressive, immunogenic conjugate of the invention, under conditions whereby the conjugate promotes the proliferation of suppressor T cells in the sample, and culturing the suppressor T cells.

In preferred embodiments of the above second aspect of the invention, the step of culturing the lymphocytes in the presence of conjugate is carried out in the presence of sufficient interleukin 2 to aid in the proliferation of the suppressor T cells; following the step of culturing the lymphocytes in the presence of the conjugate, the concentration of suppressor T cells in the sample is increased; such concentrating is carried out using an antibody specific to helper T cells to remove such cells from the sample, or using an antibody specific to the suppressor T cells to remove them from the sample so that the removed cells can be recultured; and the suppressor T cells are cultured under conditions whereby they produce the soluble immunosuppressive factor, and the method further includes recovering the immunosuppressive factor from the cultured suppressor T cells; preferably, prior to the step of culturing the suppressor T cells to produce the soluble immunosuppressive factor, the suppressor T cells are fused with myeloma cells to form hybridoma cells capable of producing the soluble immunosuppressive factor.

In a third aspect, the invention features, in general, treating a human patient suffering from SLE by administering to the patient either an effective amount of the soluble immunosuppressive factor produced by the process described above, or an effective amount of the immunosuppressive T cells described above.

In a fourth aspect, the invention features, in general, a method of treating a human patient suffering from SLE by administering to the patient an effective amount of the tolerogenic conjugate of the invention.

In a fifth aspect, the invention features, in general, a method of treating a human patient suffering from SLE by administering to the patient an effective amount of the immunosuppressive, non-immunogenic conjugate of the invention.

In an sixth aspect, the invention features, in general, a method of covalently conjugating an oligonucleotide to a carrier protein or cell including activating the oligonucleotide by reacting the oligonucleotide with glutaraldehyde and then reacting the activated oligonucleotide with the carrier protein or cell to form a conjugate.

In preferred embodiments of the above sixth aspect of the invention, activation with glutaraldehyde is carried out at a pH of 8–10.5, most preferably about 9.5, for at least 15 minutes, and the reaction of the activated oligonucleotide with the protein or cell is carried out at a pH of 8–10.5, most preferably about 9.5, at a temperature of 24°–37° C., most preferably about 37° C.

In a preferred embodiment of the above sixth aspect of the invention in which the protein is human IgG, activation using glutaraldehyde is carried out for a period of time, most preferably at least 12 hours, sufficiently long to produce activated oligonucleotide in a form which does not cause a conformational change in the IgG when the activated oligonucleotide is reacted with IgG, which conformational change would render the conjugate antigenic.

In another preferred embodiment of the above sixth aspect of the invention, in which the protein is KLH, activation using glutaraldehyde is carried out for between 5 and 40 minutes.

The invention provides treatment for SLE which addresses the immunological basis of the disease, rather than just its symptoms.

Other features and advantages of the invention will be apparent from the following description of the preferred embodiments thereof, and from the claims.

DESCRIPTION OF THE PREFERRED EMBODIMENTS

We turn now to a description of preferred embodiments of the invention, after first briefly describing the drawings.

DRAWINGS

STRUCTURE

Figure 1:
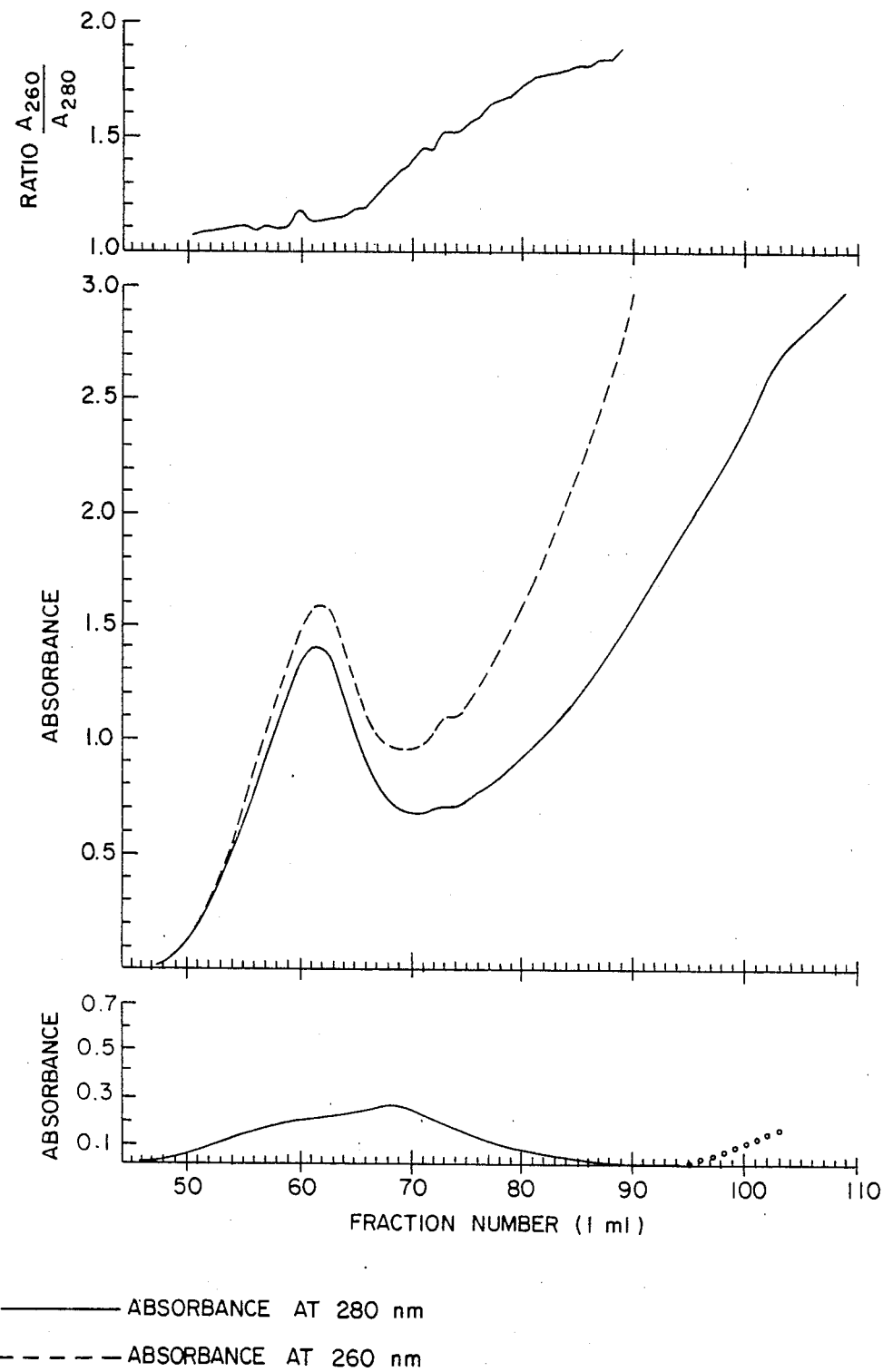
FIG. 1 is a three-part elution profile of oligonucleotide-KLH conjugate (middle panel), KLH alone (lower panel), and the A260 nm/A280 nm ratio of KLH conjugate.

The conjugates of the invention have the general structure recited in the Summary of the Invention above. Examples of preferred structures are those referred to as preferred embodiments above.

SYNTHESIS

The conjugates are prepared generally according to the methods recited in the Summary of the Invention above.

Specific conjugates were made as follows:

OLIGONUCLEOTIDE-KLH CONJUGATES

The first step in the preparation of oligonucleotide-KLH conjugates was the preparation of the heterogeneous oligonucleotides.

Commercially obtained calf thymus DNA was purified by chloroform-isoamyl alcohol extraction, ethanol precipitation, and isopropanol precipitation as described in Papalian et al. (1980) J. Clin. Invest. 65, 469. A solution of DNA (2 mg/ml) in digestion buffer (6mM Tris pH 7.6, 6mM NaCl, 6mM 2-mercaptoethanol, 6mM $NaCl_2$, pH adjusted to 7.6) was reacted with DNAse (1 unit of DNAse per 100 mg DNA) until 30% hyperchromicity was attained. The reaction was stopped by addition of 1/10 volume of 0.1 M Na EDTA. The mixture was desalted by chromatography on Sephadex G25 fine, lyophilised, and used as such or chromatographed on Ultrogel AcA44. Fractions corresponding to approximately 10-nucleotide chain lengths (as determined by the ratio of terminal to total phosphorus; Seaman (1968) Methods in Enzym. 12, 218) were pooled and lyophilised.

Another DNA fragment mixture was prepared as described above, but without separating out the 10-nucleotide chain lengths.

The next step was to activate the oligonucleotides (either the 10-nucleotide chain lengths or the mixed lengths) by mixing 119 mg of oligonucleotide in $H_2O$ with 0.1 ml of 70% glutaraldehyde, in the presence of 0.02% sodium azide. 0.2 ml of 0.15 M carbonate buffer, pH 9.6, was added and the pH was adjusted to 9.5 with 0.15 M $Na_2CO_3$, bringing the final volume to approximately 2 ml (final molarity of glutaraldehyde was 0.035 M). This solution was incubated at 37° C. for 40 min. and centrifuged to remove a white precipipate that formed during the incubation. The reaction was then stopped by chromatography on Sephadex G25 fine, equilibrated and eluated with 0.15 M carbonate buffer pH 9.5. Absorbance of the eluted fraction was measured at 260 nm. As a control, free unreacted oligonucleotides alone and glutaraldehyde alone were run separately on identical columns and their respective elution positions determined. Oligonucleotides were identified by spectrophotometry absorbance at 260 nm and glutaraldehyde by formation of a yellow color with lysine and spectrophotometry absorbance at 260 nm.

The activation of KLH using glutaraldehyde appears to cause some agglomeration of the protein, perhaps resulting in a conformational change. This could perhaps be prevented to some extent by carrying out the activation reaction for a longer period of time, e.g. twelve hours or longer, but this is not an important consideration for KLH conjugates since conformational changes if anything merely increase antigenicity, and the conjugates are intended to be highly antigenic.

The resulting elution profile gave a first peak (not shown in the Figures) corresponding to oligonucleotides activated with aldehydic groups, followed closely by a second peak corresponding to glutaraldehyde alone.

In the next step, the linkage of the activated oligonucloetides to KLH, the fractions corresponding to the first peak, above, were pooled and mixed with 30 mg KLH suspended in 0.15 M carbonate buffer, pH 9.5. The pH was adjusted to 9.5 with 0.15 M $Na_2CO_3$ and the reaction was allowed to proceed for 24 hrs. at 37° C. The appearance of yellow color was an indication of successful coupling of oligonucleotides to the protein carrier, to form oligonucleotide-KLH conjugates.

The unreacted aldehyde groups on the conjugates were then blocked by the addition of 600 mg of glycine, with the pH adjusted to 9.5 with 0.15 M carbonate buffer. The mixture was then incubated for an additional 24 hrs. at 37° C.

The solution was concentrated in Amicon stirred cells (Amicon Corp., Lexington, MA), and conjugates were then separated from unreacted oligonucleotides by filtration on Sephadex G200, particle size 40–120

μm, exclusion limit 600,000 daltons, with a 1.6×92 cm column, to which a sample volume of 4 ml was added. The column was equilibrated and eluted with 0.15 M carbonate buffered saline, pH 9.5. 1 ml fractions were collected and their optical density measured at 280 nm and 260 nm. This column was previously calibrated with KLH alone and oligonucleotides alone. The fractions corresponding to the first peak (the conjugates) were pooled and assayed for oligonucleotide by spectrophotometry at 280 nm and 260 nm and by the diphenylamine oligonucleotide assay method described in Giles et al. (1965) Nature 206, 93. Protein was determined by the Lowry method.

The final purification step employed an immunoabsorbent anti-KLH-Sepharose 4B column, prepared according to the method of March et al (1974) Analyt. Biochem. 60, 149. The first peak from the Sephadex G200 chromatography, representing the oligonucleotide-KLH conjugate, in borate-saline, pH 8.2, was applied to the anti-KLH-Sepharose column, equilibrated with the same buffer. The column was washed with the same buffer until there was no eluate containing unconjugated oligonucleotide or KLH (A280 and A260=0). The absorbed material was then eluted with 0.5 M NH4OH-HCl buffer, pH 11, containing 0.5 M NaCl. The eluate was then immediately dialysed against borate-saline, pH 8.2, concentrated, and evaluated by Lowry protein determination and spectorphotometry between 230-310 nm in parallel with KLH alone and the oligonucleotide-KLH conjugate before immunoabsorption.

Results of the above chromatography procedures are illustrated in FIG. 1. As shown therein (middle panel), chromatography of the mixture of glutaraldehyde-treated oligonucleotides and KLH on Sephadex G200 showed two distinct peaks. A first peak corresponding to the void volume contained KLH-oligonucleotide conjugates as judged by the A260:A280 ratio (1.0-1.19) in comparison with that of the same unreacted protein (0.7), and a second broad peak representing unreacted oligonucleotide with an A260:A280 ratio =1.8. The substitution attained was 5-20 oligonucleotide chains/KLH molecule, as calculated by spectrophotometry or the diphenylamine method (assuming 800,000 M.W. for KLH).

Table 1 below gives the degree of conjugation as calculated by the two methods.

TABLE 1

| MOLES OF OLIGONUCLEOTIDE COVALENTLY BOUND PER MOLE OF CARRIER PROTEIN | | |
| --- | --- | --- |
| Oligonucleotide-Protein Conjugates | Calculated by Absorbance | Direct determination by Dephenylamine Method |
| Exp. 1 | | |
| Oligonucleotide-KLH | 4.5 | 6.0 |
| Exp. 2 | | |
| Oligonucleotide-KLH | 5.9 | 7.4 |

Figure 2:
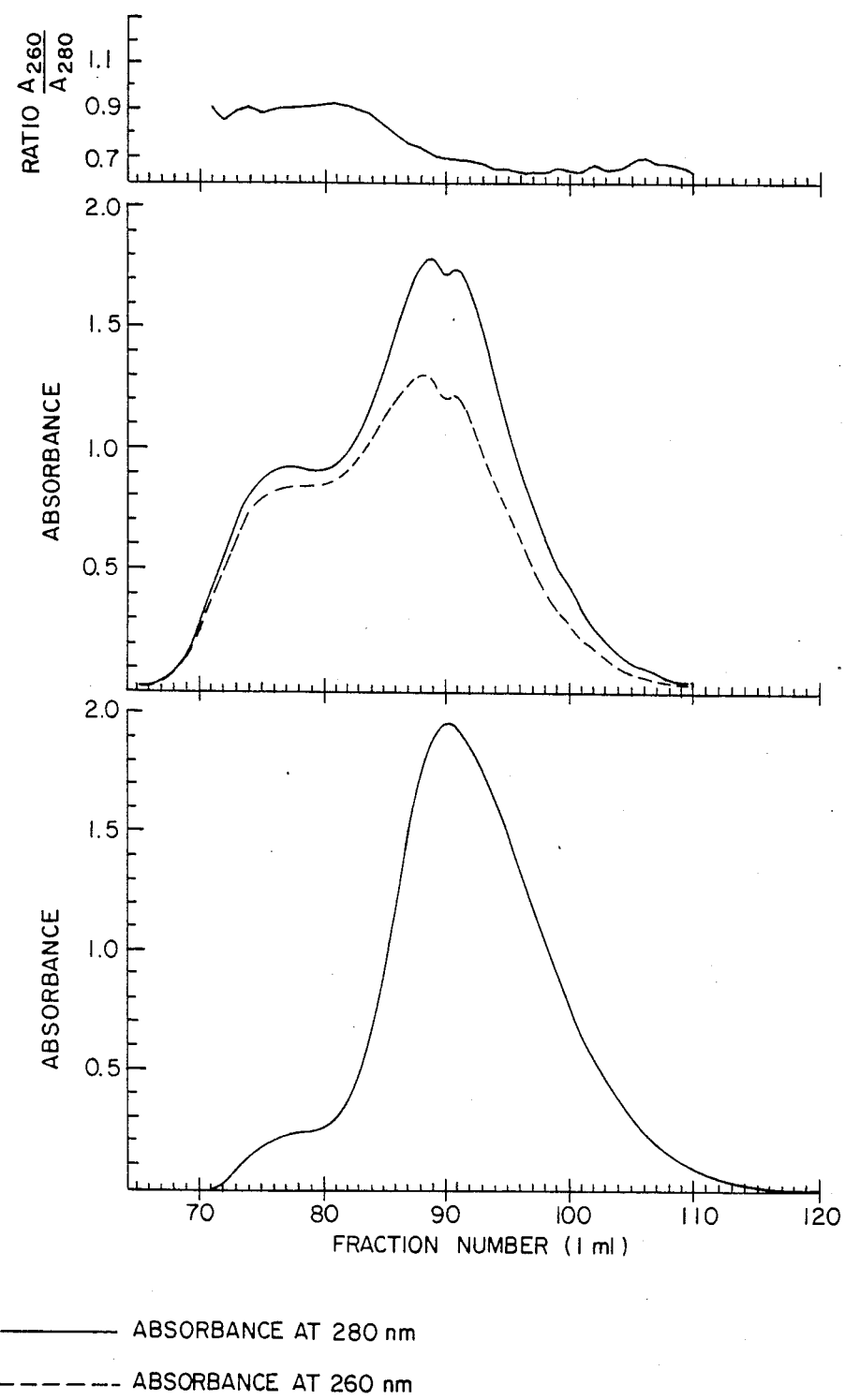
FIG. 2 is a three-part elution profile of purified oligonucleotide-IgG conjugate (middle panel), IgG alone (lower panel), and the A260 nm/A280 nm ratio of IgG conjugate.

The results of the immunoabsorbent purification procedure are illustrated in FIG. 2, which represents the absorbance spectra of the oligonucleotide-KLH conjugates isolated on Sephadex G200 before the immunoabsorption, on an anti-KLH column, the same oligonucleotide-KLH conjugate supernatant after absorption, and the eluate from the column as compared with the spectrum of KLH alone. Whereas free protein had an absorbance maximum at 280 nm, the oligonucleotide-KLH absorbed maximally at about 270 nm, combining the nucleic acid and protein spectra. This was true of the material eluted from an anti-KLH affinity column as well as the first Sephadex G200 peak, indicating that the oligonucleotide was indeed conjugated to the protein and not simply self-aggregated. Furthermore, when a sample of 0.5 mg of conjugate was applied to the anti-KLH column, all of the u.v.-absorbing material was bound to the column, indicating that virtually all of the oligonucleotide in the first Sephadex G200 fraction was bound to the KLH.

The oligonucleotide-conjugates described above are, as will be explained in more detail below, effective immunogens in SLE systems; i.e., they give rise to an immune response in vivo. These conjugates are immunogens rather than tolerogens because KLH is a foreign, antigenic protein.

OLIGONUCLEOTIDE-IGG CONJUGATES

This procedure produces not immunogens but tolerogens, i.e., conjugates which suppress the attacking of DNA by an SLE patient's own immune system. The difference between the conjugates described below and the KLH conjugates is that human IgG is an endogenous (i.e., isologous), soluble protein which, if its conformation is not significantly changed by the conjugating process, is not antigenic in humans.

The oligonucleotide-IgG conjugates were also prepared by a two step method with glutaraldehyde as a cross-linking agent as described above, with few modifications. In the first step, 17 mg of oligonucleotide was mixed with 0.15 ml of 70% glutaraldehyde. 1.4 ml of 0.15 M carbonate buffer pH 9.5 was added and pH adjusted to 9.5 with 0.15 M Na2CO3. This brought the total volume to 2 ml. The reaction mixture was mixed for about 16 hours at room temperature in the dark. The reaction was stopped by chromatography on Sephadex G25 fine as described for the immunogenic KLH conjugate.

The activation reaction was carried out for a long period of time in order to minimize agglomeration, a phenomenon associated with conformational changes in the protein. Unlike the case with immunogenic conjugates (e.g., KLH conjugates), tolerogenic conjugates should be made so that the isologous carrier protein is not changed so as to render it antigenic.

In the second step the activated oligonucleotide eluate was reacted with 17 mg of human IgG at pH 9.5 at 37° C. for 2 hours. A higher temperature was not used because denaturation of the protein was to be avoided. 230 mg of glycine were then added, the pH adjusted to 9.5, and the mixture incubated at 37° C. for 8 hours. The conjugate was then purified by affinity chromatography on Protein A-Sepharose CL-4B, using as a running buffer borate-saline pH 8, and as the elution buffer 0.5 M NaCl 0.02 M acetate pH 3.5. The conjugate-containing eluate was immediately dialysed vs borate-saline pH 8.2, concentrated by Amicon ultrafiltration, and a 4 ml sample was applied to an Ultragel AcA44 column (1.6×92 cm equilibrated and eluted with borate-saline pH 8.2), previously calibrated with unreacted identical IgG. 1 ml fractions were collected and assessed at 280 nm and 260 nm.

FIG. 3 represents the Ultrogel AcA44 elution profile of the oligonucleotide-IgG conjugate which shows a broad shoulder corresponding to the void volume, followed by an IgG peak demonstrated by comparison with a calibration profile of the same unreacted protein.

The ratio A260:A280 progressively decreased from 0.9 to 0.65, indicating an efficient separation of the different protein moieties ranging from 0.7 oligonucleotide molecules per molecule of IgG at the beginning of the peak, to mostly uncoupled IgG at the end of the IgG peak. The diphenylamine method indicated a similar degree of substitution (0.8).

OLIGONUCLEOTIDE-CELL CONJUGATE

Immunosuppressive, immunogenic conjugates are made by conjugating oligonucleotides to the surface of a heterologous (non-human) cell.

Oligonucleotides were conjugated to the surface of sheep red blood cells (SRBC) by first activating the oligonucleotide using glutaraldehyde, as described above for IgG, and then reacting the activated oligonucleotide with SRBC, without prior removal of unreacted aldehyde.

The procedure was as follows. 2-3 mg of oligonucleotide in 0.1 ml saline was mixed with 0.2 ml of 8% glutaraldehyde (Polysciences, Inc., Worthington, PA, Cat. #0216, 8% Aqueous EM grade). The pH was adjusted to 9.5 with 0.15 M carbonate buffer and the reaction was allowed to proceed at room temperature for 8 hours in the dark. 0.1 ml of a 20% cell suspension, washed and suspended in 0.15 M carbonate buffer saline pH 0.5 was added to the reaction mixture and the pH was again adjusted to 9.5 with 0.15 M $Na_2CO_3$ and left at room temperature 15-30 min. or until the color of the SRBC started to change to brown. The SRBC were then washed three times with normal saline, resuspended in a 0.1 M solution of lysine in 0.15 M carbonate buffered saline pH 9.5, incubated for 30 min. at 37° C. and washed three times with normal saline to yield purified oligonucleotide-cell conjugates.

Other conjugates can be made using methods analogous to those described above. For example, oligonucleotide can be conjugated in substantially the same way to an SLE patient's lymphocytes to make immunosuppressive, non-immunogenic conjugates.

USE

The conjugate of the invention are used according to the methods recited in the Summary of the Invention, above. All of the steps of the recited methods, e.g. the concentration of suppressor T cells in culture, and the administration of immunosuppressive conjugates, soluble immunosuppressive factor, or suppressor T cells, can be carried out using conventional, well-known techniques. The conjugates, cells, and factors of the invention which are to be administered to SLE patients will generally be first admixed with a non-toxic, pharmaceutically acceptable carrier substance. Administration will generally be intravenously, parenterally, or subcutaneously.

Dosage of the tolerogenic conjugates will vary, depending on such factors as severity of the disease, but will generally be in the range of about 1 to 250 mg/kg/day. Treatment can be carried out repeatedly, a needed.

TEST RESULTS

A procedure demonstrating the quantitative binding of KLH conjugates with anti-DNA antibody was carried out as follows. Radioactive $H^3$-DNA was purchased from New England Nuclear (Boston, MA). It was assayed with known anti-denatured DNA antibodies to rule out the presence of denatured material before it was used as native DNA. Single stranded DNA was prepared by thermal denaturation and rapid chilling of the DNA sample. A standard double antibody radioimmunoassay was used. Binding was expressed as % of total counts added. In each test, both positive and negative controls were always assayed. A positive serum was considered one that gave binding equal to or greater than the mean plus two standard deviations of the negative controls.

The degree of inhibition was expressed in percent as compared to the binding of $H^3$ DNA to SLE sera to either native or denatured DNA. Suitable concentrations of both oligonucleotide-KLH and oligonucleotide-IgG inhibited the binding of anti-DNA to native or denatured DNA, whereas unconjugated protein showed little or no inhibition. Thus, oligonucleotides bound to soluble carriers were able to bind anti-DNA antibodies from seropositive SLE sera.

The immunological activity of oligonucleotide-SRBC conjugates was demonstrated by in vitro procedures in which the conjugates exhibited hemaglutination with SLE sera.

Oligonucleotide-KLH was demonstrated to be immunogenic in procedures in which mice were immunized with the conjugate in complete Freund's adjuvant, and were found to raise either IgM or IgG anti-DNA antibodies.

Oligonucleotide-KLH conjugates were also demonstrated to be immunogenic in a human system. Cultured human lymphocytes challenged with these conjugates responded by producing anti-normal DNA antibody and anti-denatured DNA antibody.

Oligonucleotide-human $IgG_1$ conjugates, made as described above, were shown to be tolerogens in tests in which peripheral blood lymphocytes from an SLE patient were incubated both alone and in the presence of the conjugates. The spontaneous production by the cells of antibody to native DNA and to denatured (single stranded) DNA was significantly suppressed by the conjugates.

Furthermore, human lymphocytes which were pretreated by incubating them with oligonucleotide-IgG conjugate were then prevented from producing anti-DNA antibody when challenged with oligonucleotide-KLH.

MECHANISMS OF ACTION

The precise mechanism by which the oligonucleotide-IgG conjugates can induce SLE tolerance is not known. Our hypothesis is that the conjugates can block receptors on specific B cells (bone marrow derived lymphocytes) which produce the anti-DNA antibodies. The blockage of these specific receptors can induce tolerance by preventing antibody synthesis. The conjugates may also be capable of blocking receptors on helper T cells. This blockage can prevent helper T cell enhancement of antibody synthesis in B cells.

Oligonucleotide-cell conjugates can elicit immune suppression, as opposed to tolerance, by inducing the generation of suppressor T cells which suppress the development of B cells specific for nucleic acid antigens. The advantage of suppression is two fold: (a) it might suppress antibodies to a wide variety of nucleic acid antigens including native DNA; (b) it can permit the administration of a soluble factor as immunotherapy, rather than the administration of conjugates or cells.

To summarize, the primary objective of the invention is to provide antigen-specific immunotherapy for SLE by preventing or suppressing the formation of the anti-DNA antibodies which play a major role in the pathogenicity of the disease.

OTHER EMBODIMENTS

Other embodiments are within the following claims. For example, tolerogens can be made using any non-antigenic, soluble, isologous immunoglobulin, e.g. non-antigenic human IgE, IgM, IgA, and any of the IgG series. IgG is best because the Fc fragment participates in the immunoglogical functioning of the conjugates. As mentioned, the oligonucleotide can be a sample of approximately equal lengths within the suitable range, or it can be a heterogenous-length sample in that range. The sequence of the oligonucleotide is unimportant, provided that it is heterogenous. The oligonucleotide is preferably primarily (over 80%) single-stranded, since linkage of a completely double-stranded oligonucleotide is more difficult.

In the case of immunosuppressive, non-immunogenic cell conjugates, any autologous lymphocyte can be used, e.g. monocytes, spleen cells, and bone marrow cells.

In the case of immunogenic conjugates, any antigenic carrier protein can be used. Examples of suitable proteins are human serum albumin and immunoglobulins which are antigenic. Other examples are tetanus toxoid and diphtheria toxoid.

We claim:

1. A conjugate comprising an oligonucleotide covalently bonded to a carrier wherein said conjugate is a tolerogenic conjugate capable of inducing tolerance in a human patient suffering from SLE, comprising a heterogeneous DNA oligonucleotide at least 8 and not more than 500 base pairs in length covalently bonded to a non-antigenic, soluble isologous IgG immunoglobulin molecule, said covalent bonding being such that the conformation of said IgG immunoglobulin is similar enough to its natural conformation to render said conjugate tolerogenic rather than antigenic.

2. The conjugate of claim 1 wherein said IgG immunoglobulin in IgG$_1$.

3. The conjugate of claim 1 wherein said covalent bonding is via an aldehydic linkage.

4. The conjugate of claim 1 wherein each said soluble isologous IgG immunoglobulin molecule has bonded to it between 0.7 and 1.2 oligonucleotides.

* * * * *